July 25, 1972 F. W. ANDERSON Plant Pat. 3,242
ALMOND TREE
Filed Feb. 4, 1971
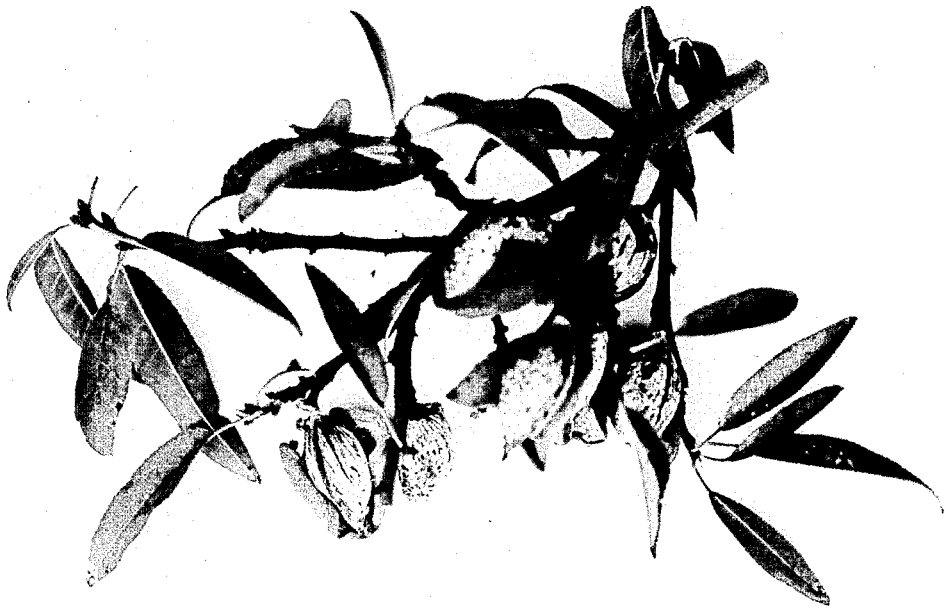
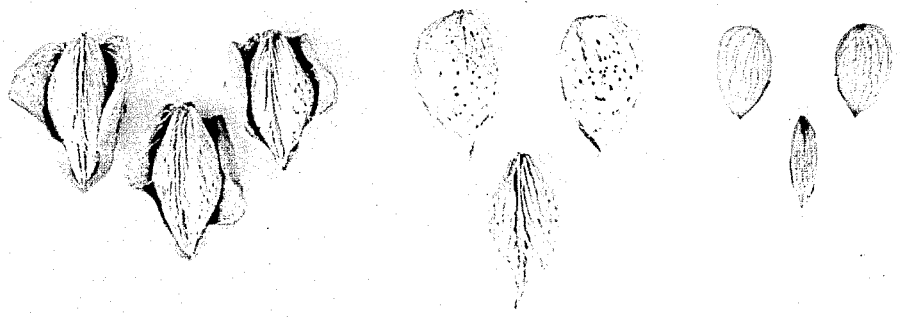
INVENTOR
Frederic W. Anderson
BY
Webster & Webster
ATTORNEYS United States Patent Office Plant Pat. 3,242
Patented July 25, 1972

3,242
ALMOND TREE

Frederic W. Anderson, Merced, Calif., assignor to Arthur Bright, Le Grand, Calif.

Filed Feb. 4, 1971, Ser. No. 112,835
Int. Cl. A01h 5/00
U.S. Cl. Plt.—30 1 Claim

ABSTRACT OF THE DISCLOSURE

An almond tree which is of large size, vigorous, open to dense, spreading to medium, abundant of foliage with large to medium size leaves, heavy of bloom with the blooming period two to three days after the Nonpareil (unpatented), and a regular bearer with heavy to medium productivity of large to medium size well-sealed nuts about the size of the IXL and Peerless (both unpatented), well distributed on the tree, and in harvest after the Nonpareil but before the Mission (unpatented) and about with the Ne Plus Ultra (unpatented).

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of nut trees. The present variety of almond tree resulted from my endeavors in the conduct of such plant breeding program.

ORIGIN OF THE VARIETY

The present variety of almond tree was originated by me in my experimental nursery and orchard, located as aforesaid, as a selection from a large progeny of seedlings which resulted from a planting of seeds from an unnamed, open-pollinated seedling of Nonpareil but which had a blooming period about two weeks later.

When the one seedling, which is the present variety, came into bearing I recognized that it was distinctively characterized in a manner advantageous for commercial growing, and I, therefore, selected such one seedling for asexual reproduction.

ASEXUAL REPRODUCTION OF THE VARIETY

After its origination by me, I asexually reproduced the present variety of almond tree by grafting the same on mature trees in my aforementioned experimental orchard, and in maturity such reproductions ran true to the original tree in all respects.

SUMMARY OF THE VARIETY

The herein claimed variety of almond tree is of large size, vigorous, open to dense, spreading to medium, abundant of foliage with large to medium size leaves, heavy of bloom with the blooming period two to three days after the Nonpareil, and a regular bearer with heavy to medium productivity of large to medium size well-sealed nuts about the size of the IXL and Peerless, well distributed on the tree, and in harvest after the Nonpareil but before the Mission and about with the Ne Plus Ultra.

As compared to the Nonpareil—long the leading almond variety grown in California—the herein claimed variety of almond tree bears nuts which have far less culls at harvest, a harder and better sealed shell, and kernels which are generally similar but of a more attractive medium light brown color, and better eating quality. As the shell is well sealed, there is substantial resistance to internal contamination by birds, insects, and dust, and to damage to the kernel by moisture.

The herein claimed variety of almond tree is further characterized by interfertility with both the Nonpareil and the Mission, as well as with the Ruby (U.S. Plant Pat. No. 1,698), Emerald (U.S. Plant Pat. No. 2,208), Norman (U.S. Plant Pat. No. 2,426), Butte (U.S. Plant Pat. No. 2,380), Ripon (U.S. Plant Pat. No. 2,379), Yosemite (U.S. Plant Pat. No. 2,534), Tioga (U.S. Plant Pat. No. 2,695), and Empire (U.S. Plant Pat. No. 2,367).

BRIEF DESCRIPTION OF THE DRAWING

The drawing is an illustration, by photographic reproduction in color, of a twig with leaves and nuts as of the time of harvest; and, separately shown, nuts in hull, nuts out of hull, and meats out of shell.

DESCRIPTION OF THE VARIETY

The botanical details of this new and distinct variety of almond tree—with color definitions (except those in common color terms) referenced to Maerz and Paul Dictionary of Color—are as follows:

Tree:
- *Size.*—Large.
- *Density.*—Open to dense.
- *Vigor.*—Vigorous.

Trunk:
- *Form.*—Medium.
- *Texture.*—Medium.

Branches:
- *Form.*—Medium.
- *Branching habit.*—Spreading to medium.

Foliage:
- *Quantity.*—Abundant.

Leaves:
- *Size.*—Large to medium. Average length: 3¼". Average width: 1⅛".
- *Shape.*—Ovate.
- *Thickness.*—Medium.
- *Texture.*—Smooth.
- *Margin.*—Crenate.
- *Petiole.*—Medium length; medium thickness.
- *Glands.*—Number: 1 to 4. Alternate; medium size; reniform; usually positioned 2 on petiole and 1 or 2 at base of blade.
- *Color.*—Top side: Medium green (22–K–7). Under side: Lighter green (22–I–6).

Bloom:
- *Amount of bloom.*—Heavy.
- *Color.*—White.
- *Blooming period.*—Medium: 2 or 3 days after Nonpareil.

Crop:
- *Bearing.*—Regular bearer.
- *Productivity.*—Heavy to medium.
- *Distribution of nuts on tree.*—Well distributed.
- *Harvest period.*—After Nonpareil but before Mission, and about with Ne Plus Ultra.
- *Tenacity.*—Tendency to drop off early; easy to harvest; easy to hull and shell.

Hull:

*Outer surface.*—Rough.
*Form.*—Regular.
*Thickness.*—Thick.
*Flesh.*—Tough.
*Dehiscence.*—Opens freely.
*Splitting.*—Along suture; freely at base.
*Color* (at maturity).—Brownish gray (14–F–6) to (15–C–4).

Nut:

*Size.*—Large to medium: About the size of IXL and Peerless. Average length: 1⅜". Average width: ⅞". Average thickness: ⅝". Average weight: Approximately 13 to an ounce.
*Form.*—Length/width: Oval. Width/thickness: Medium to flat.
*Shell.*—Hard; smooth. Outer shell: Hard. Inner shell: Hard; well sealed.
*Color.*—Straw (11–G–4).
*Pits.*—Numerous; irregular.
*Base.*—Square.
*Stem scar.*—Large.
*Apex.*—Acute; sharp.
*Wing*—Broad.
*Inner surface.*—Medium color.
*Ventral streak.*—Dark; broad.
*Percentage of kernel to nut.*—Averages approximately 45%.

Kernel:

*Size.*—Large to medium. Average length: 1". Average width: ⅝", Average thickness: ¼".
*Form.*—Length/width: Ovate. Width/thickness: Medium to flat.
*Base.*—Square to ventrally oblique.
*Stem scar.*—Small.
*Apex.*—Obtuse to acute; sharp.

*Texture.*—Smooth to slightly wrinkled.
*Pellicle.*—Thin.
*Pubescence.*—Smooth.
*Color.*—Medium light brown (13–L–8).
*Number of doubles.*—Very few.
*Defective kernels.*—Very few.
*Flavor.*—Sweet.
*Quality.*—Very good.

The almond tree and its nuts herein described may vary in slight detail due to climatic and soil conditions under which the variety may be grown; the present description being of the variety as grown in the Central Valley of California.

What is claimed is:

1. A new and distinct variety of almond tree, substantially as illustrated and described, which is of large size, vigorous, open to dense, spreading to medium, abundant of foliage with large to medium size leaves, heavy of bloom with the blooming period two to three days after the Nonpareil, and a regular bearer with heavy to medium productivity of large to medium size, well-sealed nuts about the size of the IXL and Peerless, well distributed on the tree, and in harvest after the Nonpareil but before the Mission and about with the Ne Plus Ultra; the variety being further characterized, in comparison to the Nonpareil, by less culls at havest, and by nuts having harder and better sealed shells, and more attractive medium light brown kernels of better eating quality; and the variety being additionally characterized by interfertility with the Nonpareil, Mission, Ruby, Emerald, Norman, Butte, Ripon, Yosemite, Tioga, and Empire.

No references cited.

ROBERT E. BAGWILL, Primary Examiner